(12) United States Patent
Carranza et al.

(10) Patent No.: US 8,779,122 B2
(45) Date of Patent: Jul. 15, 2014

(54) PROCESS FOR THE SYNTHESIS OF (2E)-3-(3,4-DIMETHOXYPHENYL)PROP-2-ENENITRILE, AND APPLICATION IN THE SYNTHESIS OF IVABRADINE AND ADDITION SALTS THEREOF WITH A PHARMACEUTICALLY ACCEPTABLE ACID

(71) Applicant: Les Laboratoires Servier, Suresnes Cedex (FR)

(72) Inventors: Maria Del Pilar Carranza, Villarubia De Los Ojos (ES); Maria Isabel Garcia Aranda, Toledo (ES); José Lorenzo Gonzalez, Toledo (ES); Frédéric Sanchez, Cobisa (ES)

(73) Assignee: Les Laboratoires Servier, Suresnes Cedex (FR)

( * ) Notice: Subject to any disclaimer, the term of this patent is extended or adjusted under 35 U.S.C. 154(b) by 0 days.

(21) Appl. No.: 14/073,213

(22) Filed: Nov. 6, 2013

(65) Prior Publication Data

US 2014/0128598 A1    May 8, 2014

(51) Int. Cl.
  *C07D 223/16* (2006.01)
  *C07C 255/37* (2006.01)
  *C07C 253/00* (2006.01)

(52) U.S. Cl.
  USPC ............................. 540/523; 558/357; 558/401

(58) Field of Classification Search
  USPC .................................. 540/523; 558/357, 401
  See application file for complete search history.

(56) References Cited

U.S. PATENT DOCUMENTS 5,296,482 A    3/1994 Peglion et al.

FOREIGN PATENT DOCUMENTS

| DE | 23 03 919 | 9/1973 |
| EP | 0534859 | 3/1993 |
| WO | WO 2011/138825 | 11/2011 |

OTHER PUBLICATIONS

French Preliminary Search Report for FR1260576 of Jun. 4, 2013.
Kametani Tetsuji, et al., Journal of the Chemical Society, Perkin Transactions 1, No. 10, p. 2151-2154, Jan. 1, 1985.
Spencer, A., Journal of Organometallic Chemistry, vol. 258, p. 101-108, Jan. 1, 1983.
Zhao Sheng Yin, et al.,Journal of Chemical Research, No. 7, p. 420-422, Jan. 1, 2009.

*Primary Examiner* — Bruck Kifle
(74) *Attorney, Agent, or Firm* — Hueschen and Sage

(57) ABSTRACT

Process for the synthesis of the compound of formula (I):

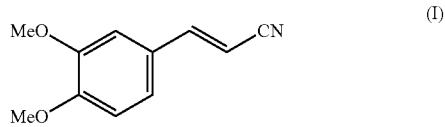

Application in the synthesis of ivabradine, addition salts thereof with a pharmaceutically acceptable acid and hydrates thereof.

14 Claims, No Drawings

PROCESS FOR THE SYNTHESIS OF (2E)-3-(3,4-DIMETHOXYPHENYL)PROP-2-ENENITRILE, AND APPLICATION IN THE SYNTHESIS OF IVABRADINE AND ADDITION SALTS THEREOF WITH A PHARMACEUTICALLY ACCEPTABLE ACID

The present invention relates to a process for the synthesis of (2E)-3-(3,4-dimethoxyphenyl)prop-2-enenitrile of formula (I):

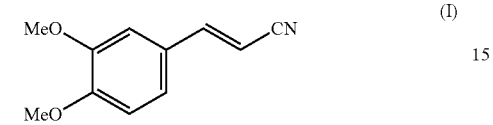

and to the application thereof in the synthesis of ivabradine and addition salts thereof with a pharmaceutically acceptable acid.

The compound of formula (I) obtained in accordance with the process of the invention is useful in the synthesis of ivabradine of formula (II):

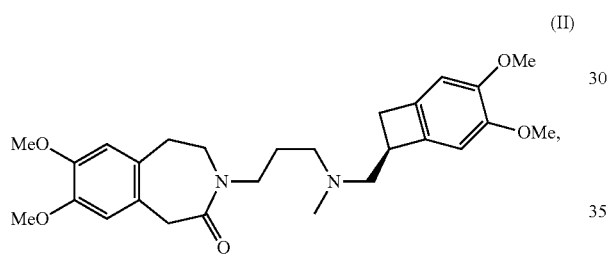

or 3-{3-[{[(7S)-3,4-dimethoxybicyclo[4.2.0]octa-1,3,5-trien-7-yl]methyl}(methyl)amino]-propyl}-7,8-dimethoxy-1,3,4,5-tetrahydro-2H-3-benzazepin-2-one,
which may be converted into an addition salt thereof with a pharmaceutically acceptable acid selected from hydrochloric acid, hydrobromic acid, sulphuric acid, phosphoric acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulphonic acid, benzenesulphonic acid and camphoric acid, and into hydrates thereof.

Ivabradine, and its addition salts with a pharmaceutically acceptable acid, and more especially its hydrochloride, have very valuable pharmacological and therapeutic properties, especially bradycardic properties, making those compounds useful in the treatment or prevention of various clinical situations of myocardial ischaemia such as angina pectoris, myocardial infarction and associated rhythm disturbances, and also in various pathologies involving rhythm disturbances, especially supraventricular rhythm disturbances, and in heart failure.

The preparation and therapeutic use of ivabradine and its addition salts with a pharmaceutically acceptable acid, and more especially its hydrochloride, have been described in the European patent specification EP 0 534 859.

That patent specification describes the preparation of ivabradine starting from 3,4-dimethoxybicyclo[4.2.0]octa-1,3,5-triene-7-carbonitrile of formula (III):

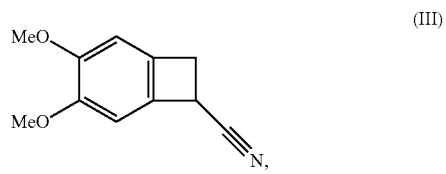 [SMILES: COc1cc2c(cc1OC)C(C#N)C2]

which is converted into the compound of formula (IV):

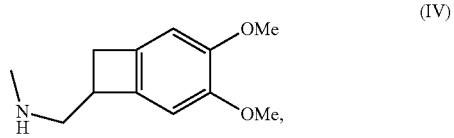

which is resolved to yield the compound of formula (V):

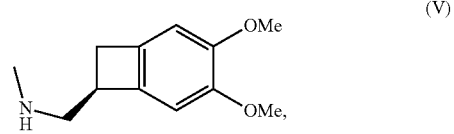

which is reacted with the compound of formula (VI):

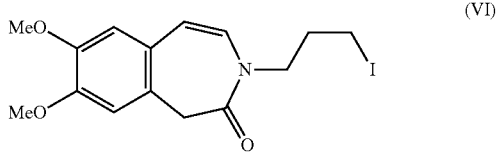 [SMILES: COc1cc2c(cc1OC)CC(=O)N(CCCI)C=C2]

to yield the compound of formula (VII):

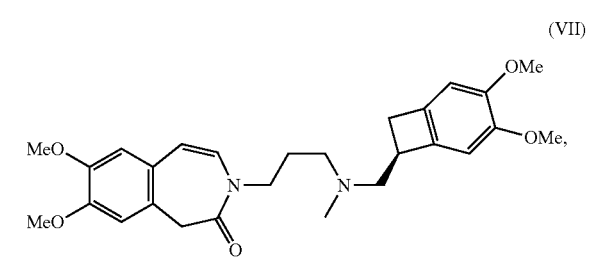 [SMILES: COc1cc2c(cc1OC)CC(=O)N(CCCN(C)C[C@H]1Cc3cc(OC)c(OC)cc31)C=C2]

the catalytic hydrogenation of which yields ivabradine, which is then converted into its hydrochloride.

The preparation of the compound of formula (III) starting from (3-(2-bromo-4,5-dimethoxyphenyl)propanenitrile of formula (VIII) is described in *Tetrahedron* 1973, 29, pp 73-76:

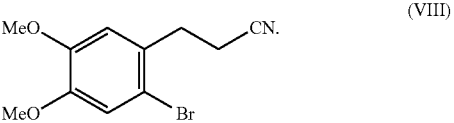 [SMILES: COc1cc(Br)c(CCC#N)cc1OC]

The compound of formula (I), a precursor of the compound of formula (VIII), is accordingly a key intermediate in the synthesis of ivabradine.

The patent application DE 2 303 919 describes the preparation of the compound of formula (I), starting from 3,4-dimethoxybenzaldehyde, with a yield of 74%.

In view of the industrial value of ivabradine and its salts, it has been imperative to find an effective process allowing (2E)-3-(3,4-dimethoxyphenyl)prop-2-enenitrile of formula (I) to be obtained in an excellent yield.

The present invention relates to a process for the synthesis of the compound of formula (I):

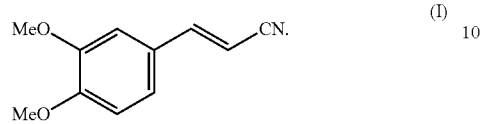

characterised in that the compound of formula (IX):

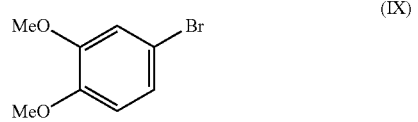 [SMILES: COc1ccc(Br)cc1OC]

is subjected to a coupling reaction with acrylonitrile in the presence of a palladium catalyst, a ligand, a base and a phase transfer agent in an organic solvent to yield the compound of formula (I).

Among the palladium catalysts that may be used to carry out the conversion of the compound of formula (IX) into the compound of formula (I), there may be mentioned, without implying any limitation, palladium(II) acetate, palladium on carbon, and palladium(II) chloride.

The palladium catalyst preferably used to carry out the conversion of the compound of formula (IX) into the compound of formula (I) is palladium on carbon.

Among the ligands that may be used to carry out the conversion of the compound of formula (IX) into the compound of formula (I), there may be mentioned, without implying any limitation, triphenylphosphine and tri(o-tolyl)phosphine.

The ligand preferably used to carry out the conversion of the compound of formula (IX) into the compound of formula (I) is tri(o-tolyl)phosphine.

Among the bases that may be used to carry out the conversion of the compound of formula (IX) into the compound of formula (I), there may be mentioned, without implying any limitation, triethylamine, sodium acetate, sodium carbonate and potassium carbonate.

The base preferably used to carry out the conversion of the compound of formula (IX) into the compound of formula (I) is sodium acetate.

Among the phase transfer agents that may be used to carry out the conversion of the compound of formula (IX) into the compound of formula (I), there may be mentioned, without implying any limitation, tetrabutylammonium bromide and tetrabutylammonium chloride.

The phase transfer agent preferably used to carry out the conversion of the compound of formula (IX) into the compound of formula (I) is tetrabutylammonium bromide.

Among the organic solvents that may be used to carry out the conversion of the compound of formula (IX) into the compound of formula (I), there may be mentioned, without implying any limitation, N,N-dimethylacetamide and N,N-dimethylformamide.

The solvent preferably used to carry out the conversion of the compound of formula (IX) into the compound of formula (I) is N,N-dimethylacetamide.

The conversion of the compound of formula (IX) into the compound of formula (I) is carried out at a temperature preferably between 100° C. and 170° C., inclusive.

The present invention relates also to a process for the synthesis of the compound of formula (VIII) starting from the compound of formula (I), prepared according to the process described hereinbefore, characterised in that said compound of formula (I):

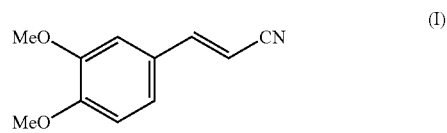 [SMILES: COc1ccc(/C=C/C#N)cc1OC]

is converted into the compound of formula (X):

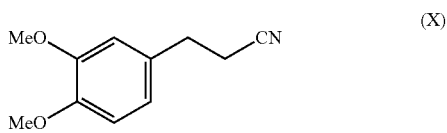 [SMILES: COc1ccc(CCC#N)cc1OC]

by a reduction reaction, which compound is converted into the compound of formula (VIII):

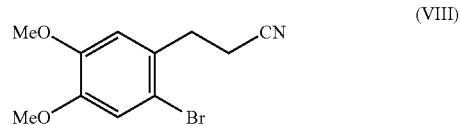 [SMILES: COc1cc(Br)c(CCC#N)cc1OC]

by a bromination reaction.

The reduction reaction performed on the compound of formula (I) may be carried out under the conditions described for the corresponding brominated compound in the patent application CN 101 407 474 and in the publication *J. Chem. Res.* 2009 (7), 420-422.

The bromination reaction performed on the compound of formula (X) may be carried out under the conditions described for similar compounds in the publications *J. Chem. Soc., Perkin Trans I* 1985, 2151-2154 and *J. Chem. Soc., Perkin Trans I* 1991, 1749-1754.

Also, the preparation of the compound of formula (VIII) by a bromination reaction performed on the compound of formula (X), in the presence of dibromine in acetic acid, has been described in *J. Org. Chem* 1972, vol. 37, no. 21, pp 3374-3376, with a yield of 48%.

The present invention relates also to a process for the synthesis of ivabradine starting from the compound of formula (I) prepared in accordance with the process of the invention and converted into the compound of formula (VIII) in accordance with the reaction sequence described hereinbefore. The compound of formula (VIII) is then converted into the compound of formula (III) following the teaching of the prior art (*Tetrahedron* 1973, 29, pp 73-76) by an intramolecular cyclisation reaction in a basic medium, said compound of formula (III) then being converted into ivabradine in accordance with the process described in EP 0 534 859.

The Examples that follow illustrate the invention.

The melting points were measured using a BÜCHI B-545 Melting Point Apparatus (Volt. 230 VAC, Freq. 50/60 Hz, Power max. 220 W).

LIST OF ABBREVIATIONS USED

DMAC: N,N-dimethylacetamide
m.p: melting point
THF: tetrahydrofuran

EXAMPLE 1

(2E)-3-(3,4-dimethoxyphenyl)prop-2-enenitrile

A mixture of 5 g of 4-bromo-1,2-dimethoxybenzene (3.31 mL, 23 mmoles), 3.2 g of acrylonitrile (3.9 mL, 60 mmoles, 2.6 eq.), 2.3 g of sodium acetate (27.6 mmoles, 1.2 eq.), 7.4 g of tetrabutylammonium bromide (23 mmoles, 1 eq.), 0.7 g of tri(o-tolyl)phosphine (2.3 mmoles, 0.1 eq.) and 4.9 g of palladium 5% on carbon (2.3 mmoles, 0.1 eq.) in 25 mL of DMAC is prepared. The black suspension is stirred at reflux for 12 hours. The reaction mixture is brought back to ambient temperature and filtered. The solid residue is rinsed twice with toluene. The filtrates are combined and evaporated under reduced pressure. The crude reaction product is purified on a silica column (eluant: methylcyclohexane:ethyl acetate 6:4) to yield 1.4 g of the expected product.
Yield=33%
m.p.=92-99° C.

EXAMPLE 2

3-(3,4-dimethoxyphenyl)propanenitrile

To a solution of 1 g (5.3 mmoles) of (2E)-3-(3,4-dimethoxyphenyl)prop-2-enenitrile in 9.3 mL of pyridine and 2.8 mL of methanol there is added, little by little, 0.24 g of NaBH$_4$ (6.3 mmol, 1.2 eq.). The reaction mixture is heated at reflux for 9 hours. After cooling to ambient temperature, the reaction mixture is added to a solution of 9 mL of hydrochloric acid 37% in 24 g of ice. The solution is extracted twice with dichloromethane. The organic phases are collected and the solvent is evaporated off under reduced pressure to yield 0.82 g of a red-brown oil which crystallises.
Yield=82%
m.p.=47-48° C.

EXAMPLE 3

3-(2-bromo-4,5-dimethoxyphenyl)propanenitrile

Preparation of the title compound is based on the procedure described in the publication *J. Chem. Soc., Perkin Trans I* 1985, 2151-2154 for preparation of 3-(2-bromo-5,6-dimethoxyphenyl)propanenitrile):

To a mixture of 21 g of 3-(3,4-dimethoxyphenyl)propanenitrile, 10.3 g of sodium acetate and 400 mL of acetic acid there are added 20 g of dibromine in 50 mL of acetic acid. The resulting reaction mixture is stirred overnight and then poured into water and extracted with benzene. The organic phase is washed with aqueous sodium thiosulphate solution and then with water, dried over sodium sulphate and concentrated under reduced pressure. The crude reaction product is purified on a silica column (eluant: benzene), and the product obtained is recrystallised from ethanol to yield 19.3 g of the expected product.
Yield=65%
m.p.: 78-80° C.

EXAMPLE 4

3,4-dimethoxybicyclo[4.2.0]octa-1,3,5-triene-7-carbonitrile

Based on *Tetrahedron* 1973, 29, pp 73-76

To a solution of NaNH$_2$, prepared starting from 200 mL of liquid NH$_3$ and 1 g of Na (catalyst: FeCl$_3$) there are added, in portions, 5.4 g of 3-(2-bromo-4,5-dimethoxyphenyl)propanenitrile and the reaction mixture is stirred at ambient temperature for 2 hours. After evaporating off the excess NH$_3$, 2 g of NH$_4$Cl and 200 mL of water are added in portions. The grey crystals formed are collected and recrystallised from ethanol to yield 2.38 g of the expected product.
Yield=74%
m.p.=84-85° C.

EXAMPLE 5

3,4-dimethoxy-N-methylbicyclo[4.2.0]octa-1,3,5-trien-7-amine

Based on EP 0 534 859

Step 1: 3,4-dimethoxybicyclo[4.2.0]octa-1,3,5-trien-7-amine hydrochloride 312 mL of a molar solution of borane complexed with THF are added dropwise, and whilst stirring at ambient temperature, to a solution of 25 g of 3,4-dimethoxybicyclo[4.2.0]octa-1,3,5-triene-7-carbonitrile in 250 mL of THF and left in contact for 12 hours; 200 mL of ethanol are then added and stirring is carried out for 1 hour. 100 mL of 3.3N ethereal HCl are added dropwise. 27.7 g of the expected product are obtained.
Yield=90%
m.p.=205° C.

Step 2: ethyl (3,4-dimethoxybicyclo[4.2.0]octa-1,3,5-trien-7-yl)carbamate 1.5 mL of ethyl chloroformate are poured into a suspension of 3.4 g of the compound obtained in Step 1 in 4.5 mL of triethylamine and 50 mL of dichloromethane and left overnight, whilst stirring at ambient temperature; washing with water and with 1N hydrochloric acid is then carried out. Drying is carried out and the solvent is evaporated off to dryness. 3.2 g of an oil corresponding to the expected product are obtained.
Yield=80%

Step 3: 3,4-dimethoxy-N-methylbicyclo[4.2.0]octa-1,3,5-trien-7-amine 3.2 g of the compound obtained in Step 2 dissolved in 30 mL of THF are added to a suspension of 0.9 g of LiAlH$_4$ in 20 mL of THF. Refluxing is carried out for 1 hour 30 minutes, then hydrolysing using 0.6 ml of water and 0.5 mL of 20% sodium hydroxide solution and, finally, 2.3 mL of water. The mineral salts are then filtered off, rinsed with THF and then the filtrate obtained is evaporated to dryness. 2.3 g of the expected compound are obtained.
Yield=92%

EXAMPLE 6

(7S)-3,4-dimethoxy-N-methylbicyclo[4.2.0]octa-1,3,5-trien-7-amine

Based on EP 0 534 859

3,4-Dimethoxy-N-methylbicyclo[4.2.0]octa-1,3,5-trien-7-amine is reacted with an equimolar amount of (d) camphorsulphonic acid in ethanol. After evaporating off the solvent in vacuo, the salt is recrystallised first from ethyl acetate and then from acetonitrile until the target enantiomer is obtained with an optical purity of more than 99% (evaluated by HPLC on a Chiralcel® OD column).

EXAMPLE 7

3-{3-[{[(7S)-3,4-dimethoxybicyclo[4.2.0]octa-1,3,5-trien-7-yl]methyl}-(methyl)amino]propyl}-7,8-dimethoxy-1,3-dihydro-2H-3-benzazepin-2-one Based on EP 0 534 859

A solution of the (d) camphorsulphonate salt obtained in Example 6 in ethyl acetate is brought to basic pH using sodium hydroxide and then the organic phase is separated off, washed, dried over $Na_2SO_4$ and evaporated.

A mixture composed of 5.6 g of potassium carbonate, 2.2 g of the above amine in 100 mL of acetone and 4 g of 3-(3-iodopropyl)-7,8-dimethoxy-1,3-dihydro-2H-3-benzazepin-2-one is then refluxed for 18 hours.

The solvent is evaporated off in vacuo, and the residue is taken up in ethyl acetate and then extracted with 3N hydrochloric acid.

The aqueous phase separated off is brought to basic pH using sodium hydroxide and is then extracted with ethyl acetate. After washing until neutral and drying over $MgSO_4$, evaporation in vacuo is carried out to obtain 4.5 g of an oil which is purified on a silica column using a mixture of dichloromethane/methanol (90/10) as eluant.

Yield=64%

EXAMPLE 8

3-{3-[{[(7S)-3,4-dimethoxybicyclo[4.2.0]octa-1,3,5-trien-7-yl]methyl}-(methyl)amino]propyl}-7,8-dimethoxy-1,3,4,5-tetrahydro-2H-3-benzazepin-2-one Based on EP 0 534 859

5 g of 3-{3-[{[(7S)-3,4-dimethoxybicyclo[4.2.0]octa-1,3,5-trien-7-yl]methyl}(methyl)-amino]propyl}-7,8-dimethoxy-1,3-dihydro-2H-3-benzazepin-2-one in 50 mL of glacial acetic acid are hydrogenated in a Parr apparatus under a hydrogen pressure of 4.9 bar at ambient temperature for 24 hours in the presence of 1 g of palladium hydroxide 10%. The catalyst is filtered off, the solvent is evaporated off, and then the dry residue is taken up in water and ethyl acetate. The organic phase is dried over anhydrous magnesium sulphate, concentration in vacuo is carried out and then the residue is purified on a silica column using a mixture of dichloromethane/methanol (95/5) as eluant.

After recrystallisation from ethyl acetate, 2 g of the expected compound are obtained.

Yield=40% m.p.=101-103° C.

The invention claimed is:

1. A process for the synthesis of a compound of formula (I):

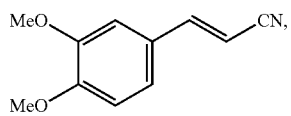

wherein the compound of formula (IX):

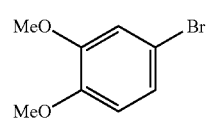

is subjected to a coupling reaction with acrylonitrile in the presence of a palladium catalyst, a ligand, a base and a phase transfer agent in an organic solvent to yield the compound of formula (I).

2. The process according to claim 1, wherein the palladium catalyst used to carry out the conversion of the compound of formula (IX) into the compound of formula (I) is selected from palladium(II) acetate, palladium on carbon, and palladium(II) chloride.

3. The process according to claim 2, wherein the palladium catalyst used to carry out the conversion of the compound of formula (IX) into the compound of formula (I) is palladium on carbon.

4. The process according to claim 1, wherein the ligand used to carry out the conversion of the compound of formula (IX) into the compound of formula (I) is selected from triphenylphosphine and tri(o-tolyl)phosphine.

5. The process according to claim 4, wherein the ligand used to carry out the conversion of the compound of formula (IX) into the compound of formula (I) is tri(o-tolyl)phosphine.

6. The process according to claim 1, wherein the base used to carry out the conversion of the compound of formula (LX) into the compound of formula (I) is selected from triethylamine, sodium acetate, sodium carbonate and potassium carbonate.

7. The process according to claim 6, wherein the base used to carry out the conversion of the compound of formula (IX) into the compound of formula (I) is sodium acetate.

8. The process according to claim 1, wherein the phase transfer agent used to carry out the conversion of the compound of formula (IX) into the compound of formula (I) is selected from tetrabutylammonium bromide and tetrabutylammonium chloride.

9. The process according to claim 8, wherein the phase transfer agent used to carry out the conversion of the compound of formula (IX) into the compound of formula (I) is tetrabutylammonium bromide.

10. The process according to claim 1, wherein the organic solvent used to carry out the conversion of the compound of formula (IX) into the compound of formula (I) is selected from N,N-dimethylacetamide and N,N-dimethylformamide.

11. The process according to claim 10, wherein the organic solvent used to carry out the conversion of the compound of formula (IX) into the compound of formula (I) is N,N-dimethylacetamide.

12. The process according to claim 1, wherein the conversion of the compound of formula (IX) into the compound of formula (I) is carried out at a temperature between 100° C. and 170° C., inclusive.

13. The process according to claim 1, wherein the compound of formula (I) obtained is subsequently converted into a compound of formula (X):

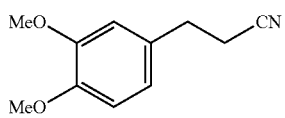

by a reduction reaction, which compound of formula (X) is converted into the compound of formula (VIII):

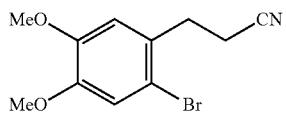

by a bromination reaction.

14. A process for the synthesis of ivabradine, or a pharmaceutically acceptable salt thereof, wherein:

a compound of formula (IX)

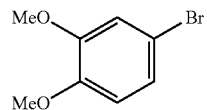

is subject to a coupling reaction with acrylonitrile in the presence of a palladium catalyst, a ligand, a base and a phase transfer agent in an organic solvent to yield a compound of formula (I)

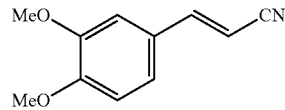

the compound of formula (I) is subsequently converted into a compound of a compound of formula (X):

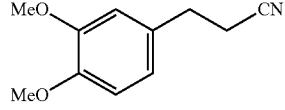

by a reduction reaction, which compound of formula (X) is converted into a compound of formula (VIII):

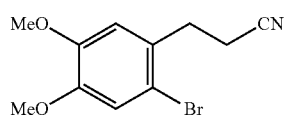

by a bromination reaction;

the compound of formula (VIII) is subjected to an intramolecular cyclization reaction in a basic medium to yield a compound of formula (III):

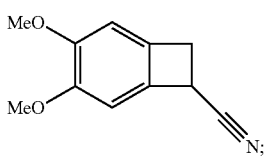

the compound of formula (III) is subject to reduction conditions to yield a compound of formula (IV):

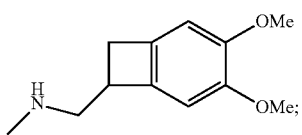

the compound of formula (IV) is subjected to optical resolution conditions to yield a compound of formula (V);

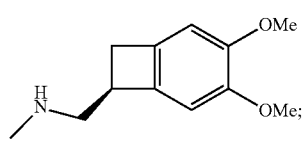

the compound of formula (V) is reacted with a compound of formula (VI):

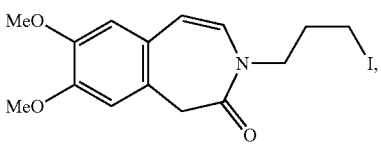

to yield a compound of formula (VII):

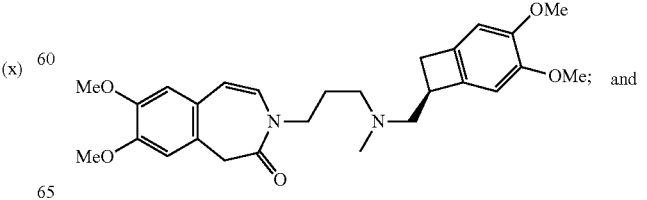

and the compound of formula (VII) is subjected to catalytic hydrogenation conditions to yield ivabradine, which may optionally be converted into an addition salt thereof with a pharmaceutically acceptable acid selected from hydrochloric acid, hydrobromic acid, sulphuric acid, phosphoric acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulphonic acid, benzenesulphonic acid and camphoric acid.

* * * * *

UNITED STATES PATENT AND TRADEMARK OFFICE
CERTIFICATE OF CORRECTION

| | | |
|---|---|---|
| PATENT NO. | : 8,779,122 B2 | Page 1 of 1 |
| APPLICATION NO. | : 14/073213 | |
| DATED | : July 15, 2014 | |
| INVENTOR(S) | : Carranza et al. | |

It is certified that error appears in the above-identified patent and that said Letters Patent is hereby corrected as shown below:

On the Title Page, Item [75]: delete "Villarubia" and insert --Villarrubia--.

On the Title Page, Item [30]: delete "WO 2011/138825" and insert --WO 2011/138625--.

In the Claims

Column 8, Line 43, Claim 6: delete "(LX)" and insert --(IX)--.

Column 9, Line 43, Claim 14: delete "subject" and insert --subjected--.

Signed and Sealed this
Fourth Day of November, 2014

Michelle K. Lee
*Deputy Director of the United States Patent and Trademark Office*